United States Patent [19]

Lang

[11] 4,094,740

[45] June 13, 1978

[54] PREPARATION OF LIQUID FUEL AND NUTRIENTS FROM SOLID MUNICIPAL WASTE

[76] Inventor: John L. Lang, P.O. Box 1242, Midland, Mich. 48640

[21] Appl. No.: 509,812

[22] Filed: Sep. 27, 1974

[51] Int. Cl.² .............................................. C12C 1/00
[52] U.S. Cl. ........................................ 195/27; 71/14;
    127/36; 195/32; 195/100; 426/7; 426/53;
    426/56
[58] Field of Search ................. 195/100, 32, 28 R, 33,
    195/34, 82, 91, 31 P, 27; 210/13, 42, 44, 73, 11,
    63; 110/8 P; 71/14; 127/36; 426/7, 53, 56

[56] References Cited

U.S. PATENT DOCUMENTS

| 2,123,211 | 7/1938 | Scholler ................................. 195/33 |
| 3,676,334 | 7/1972 | Zukerman et al. ................. 210/11 X |
| 3,711,392 | 1/1973 | Metzger ............................. 210/11 X |
| 3,725,538 | 4/1973 | Brewer ............................. 110/8 P X |

*Primary Examiner*—R. B. Penland

[57] ABSTRACT

The organic portion of solid municipal waste is converted into a liquid fuel suitable for use in internal- and external-combustion engines, a residue suitable for plant or animal nutrients and purified water by the process which comprises separation of the waste into a hydrolyzable fraction, hydrolysis of said fraction, saccharification, fermentation, distillation, and concentration.

8 Claims, 1 Drawing Figure

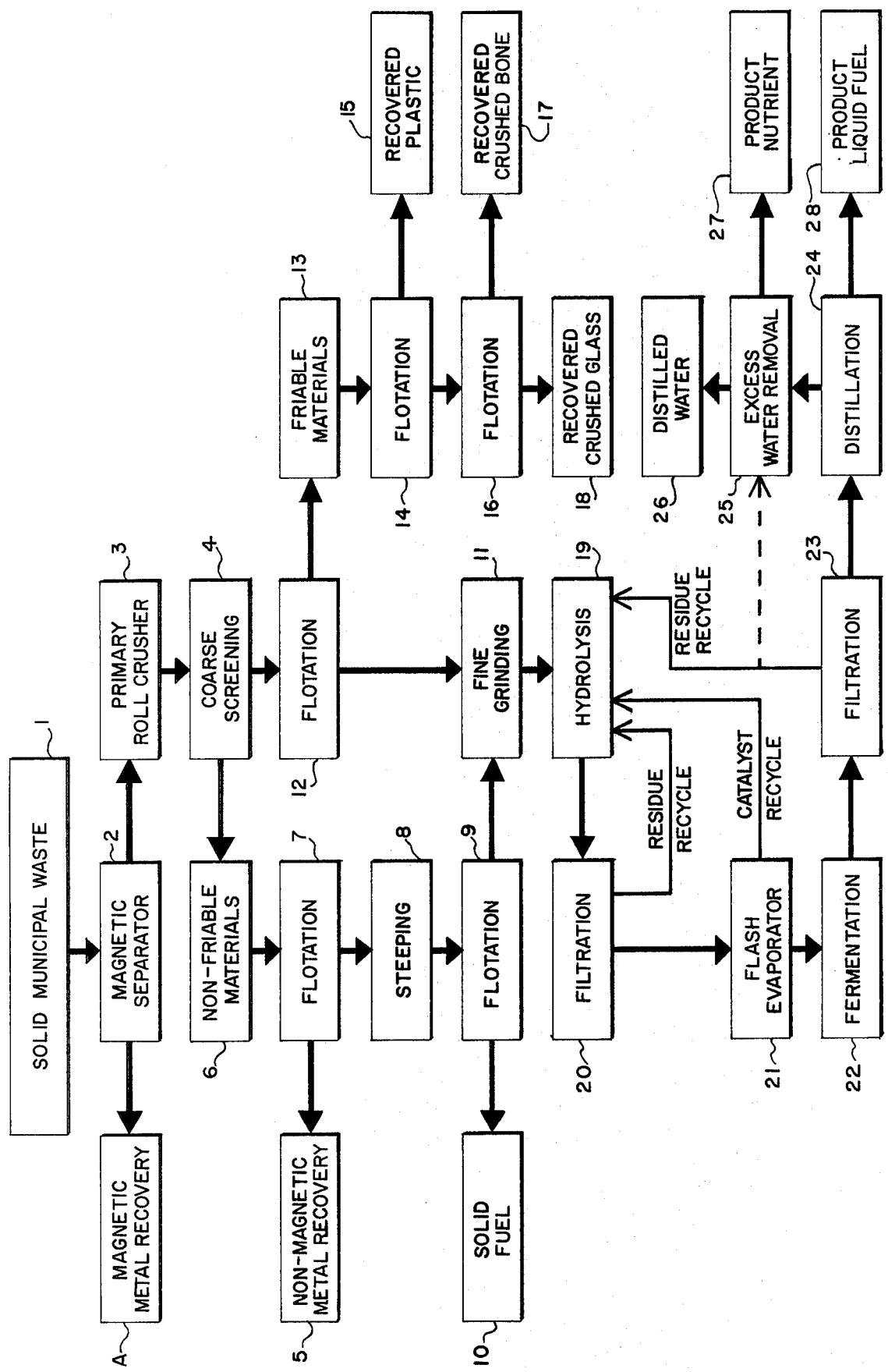

PREPARATION OF LIQUID FUEL AND
NUTRIENTS FROM SOLID MUNICIPAL WASTE

BACKGROUND OF THE INVENTION

The problem involved in disposal of solid municipal waste (garbage) is presently solved by the so-called "sanitary landfill" method, incineration, disposal in abandoned mines, merely dumping, etc.

These methods are wasteful, in terms of the loss of the energy content of such materials, the dissemination of otherwise valuable resources, and in the case of incineration, the loss of the energy stored as carbohydrates and fixed nitrogen compounds represents a fearful waste, as these materials have to be resynthesized by either nature or man in order to replace the supply of foodstuffs available to the human race.

Several attempts have been made to recover at least a part of the energy values in such materials by rather exotic processes, e.g., the hydrogenation thereof under conditions of high temperatures and pressures, by direct gasification, by drying and burning them together with other fossil fuels in electrical power houses, etc. The disadvantages of such systems include high capital investments for special reactors, the production of considerable char instead of the primary fuel product, and the necessity for special flue-gas purification systems in order to meet air-purity standards.

SUMMARY OF THE INVENTION

This invention concerns a disposal method for solid municipal waste which recovers therefrom the re-cyclable materials therein, such as glass, metals, plastics, bones, etc., and in addition converts the major portion of organic components of the waste into liquid fuel, and plant-and animal-nutrients.

This process comprises the combined steps of separation of non-hydrolyzable materials from said waste followed by conversion of said separated solid components of said waste to a fermentable mixture, fermentation of said fermentable mixture, and separation of the end products of the fermentation to produce a valuable nutrient fraction and a valuable fuel fraction, e.g. as fuel for an internal combustion engine, as a source of other forms of energy such as electrical power or heat.

Thus the object of this invention is to both provide a means for the ultimate disposal of municipal waste and simultaneously produce therefrom liquid fuel, high nitrogenous-content nutrients, and purified water.

Another object of this invention is to provide for the ultimate disposal of municipal waste in a useful form, in contrast with the conventional methods.

A further object of this invention is to provide a liquidous fuel, suitable for use in heating, and electric power generation.

Another object of this invention is to provide a liquidous fuel suitable for use in an internal combustion engine.

An additional object of this invention is the preparation of a nutrient for other useful microorganisms.

MORE PARTICULAR DESCRIPTION OF THE INVENTION

The steps of the process are comprised essentially of those outline in FIG. 1. The solid municipal waste 1 is passed through a magnetic separator, and the magnetically susceptible materials (A) therein removed for recovery by step 2, and the non-magnetically susceptible mixture sent to Primary Roll Crusher step 3, wherein friable materials are crushed, including certain plastics, bone and vegetable materials, and the non-magnetically susceptible metals, leather, tough plastics, etc., are merely flattened. The crushed mixture is put through Coarse Screening step 4, in which the crushed material passes through the screen thereof, and the tough materials do not. This step is arranged to separate the non-friable materials 6 from the mixture. The non-friable material in the solid waste is put through Flotation step 7, which separates the non-magnetically susceptible metals (5) for recovery. The balance of the non-friable materials is subjected to Steeping (step 8) during which the hydrolyzable materials become preferentially heavier by absorption of water and sink, while the non-friable plastic films, waxed paper, etc., do not absorb water and hence float. These materials are separated in Flotation step 9; the floating materials may be superficially dried and used as a Product solid fuel (10). The sinking material is sent to the Fine Grinding step 11. The material passing through the screen of step 4, is separated by Flotation step 12 into a heavier fraction containing crushed friable plastics, crushed bone, and crushed glass and a lighter fraction containing hydrolyzable materials which are sent to Fine Grinding step 11. The heavier fraction of friable materials (13) are processed by a Flotation step 14, wherein specific gravity of the fluid is adjusted to so that the friable plastics float and the glass and bone fragments sink. The Recovered Plastic 15 results; the mixture of glass and bone fragments is then subjected to Flotation step 16, wherein the specific gravity of the fluid is adjusted so that the bone fragments float and the glass fragments sink, thus separating for recovery the Recovered Crushed Bone 17 and the Recovered Crushed Glass 18.

After the hydrolyzable materials of the original solid municipal waste from steps 9 and 12 have passed through the Fine Grinding (step 11) they are forwarded to the Hydrolysis step 19, wherein a significant portion of the hydrolyzables are saccharified to fermentable sugar-like materials. This saccharified and optionally carmelized materials is filtered in step 20; the residue is recycled to the hydrolysis step 19; the filtrate from step 20 is flash evaporated in step 21 removing excess volatiles, including gaseous hydrolysis catalysts if used in step 19, and concentrating the filtrate to the desired volume and/or solids content. This mixture is sent to fermentation step 22, where appropriate addition of microorganisms and/or enzyme-containing materials and maintainance of proper conditions of time, temperature and pH brings about conversion of the fermentables to the desired fermentation products.

After fermentation 22, the material is filtered in step 23; the residue is again optionally recycled to hydrolysis step 19 or to Excess Water Removal step 25, depending upon the work load of the hydrolyzer 19 or the supply-demand circumstances for product nutrient 27.

The filtrate is forwarded to Distillation step 24, and the overhead liquid fuel product 28 collected for use.

The residue from distillation step 24 is sent to Excess Water Removal step 25, where it and the residue from Filtration step 23 are de-watered to a consistency suitable for use as animal and/or plant nutrients; partial de-watering giving a syrupy product suitable for use as a binder for other nutrients as grains, peat moss, etc., and the resulting mixture flaked, pelletized or as otherwise preferred for nutrient as a Product Nutrient 27, or de-watered to a concentration suitable for use per se as Product Nutrient 27.

The water removed in Excess Water Removal step 25 is Distilled Water 26, a known marketable commodity.

The following Example is given merely to illustrate the invention, and is not to be construed as limiting the claims in any way.

EXAMPLE I

A representative "synthetic" solid municipal waste was prepared by mixing fat, meat scraps, paper, cabbage leaves, carrot tops, potato peelings, bones, polyethylene film, aluminum foil, glass, tinned iron sheet metal, bottle caps and leather.

This synthetic solid waste, when passed through magnetic separator, results in the removal of the magnetic materials therein for recovery. The non-magnetically susceptible materials thus separated, when passed through a roll crusher, results in considerable size reduction of the friable materials therein, including most of the materials derived from vegetable and animal sources, the brittle plastics, bones and glass; this roll crusher merely flattens the non-magnetically susceptible metals, the flexible plastic films, and the tougher components such as leather, gristle, etc. of the waste.

The crushed material, when passed through a coarse screen, is separated into a portion which contains the non-magnetic metals, flexible plastics, and the tough components such as leather, paper, etc. and another portion containing the softer animal and vegetable materials, friable plastics, bone, glass, etc.

The non-friable portion when subjected to a brine flotation of sp. gr. of 1.2 is separated into a sinking fraction which contains the non-magnetically susceptible metals, which are thereby recovered. The floating fraction is subjected to a steeping process for at least 4 hours; the water-susceptible materials, such as leather, paper, cloth, etc. absorb water and sink. A successive flotational separation this separates the water-repellent materials such as plastic films, rubber, etc.

The floating fraction is used as solid fuel or recovered as desired, while the sinking portion is separated and contains the leather, gristle, paper, etc., which is put through a fine grinder of the chopper type.

The friable material from the roll crusher, after the screen separation thereof, when subjected to a flotation step using water, results in separation of a slurry of the main animal and vegetable parts of the original waste and a settled mixture of friable plastic, bone, glass, etc.

The slurry of animal and vegetable matter is sent to the fine grinder-chopper, while the sedimented material is gravity separated by flotation into recovered friable plastic granules, bone granules, and glass fragments.

After the fine grinding of this separated animal and vegetable material, this mixture was subjected to a hydrolysis step, using sulfurous acid as a catalyst.

The saccharified material was cooled and concentrated by passing through a falling-film evaporator, operated so that the effluent temperature was 65° C and the organic solids content was about 30%. The pH was adjusted to a value of 3.4, and a small amount of enzymes, e.g., in the form of barley malt, was added. This enzyme-containing mixture was maintained at 65° C for 3 hours.

After cooling to 27° C and re-adjustment of the pH to a value of 3.4, yeast was added and the temperature and pH maintained until fermentation ceased. The fermented material was filtered, the residuum steam sterilized and stored. The filtrate was distilled, using a 4-foot column packed with porcelain chips, fitted with a take-off head which was regulated at a reflux-ratio of 20:1. The still-pot heating was regulated to maintain a temperature in the vicinity of 76°–80° C at the still head.

Based upon an initial charge of 100 parts to the still-pot, the distillate was about 11 parts of ethanol-water mixture. The ethanol was, optionally, dried with calcium oxide, filtered and this product mixed 1:9 with gasoline. This liquid fuel mixture, after minor carburetor adjustment, was found to burn cleanly and well in a conventional internal combustion engine.

The filtered residuum from the fermentation step was re-combined with the still-pot residuum, and the whole evaporated until a thick syrup was formed, distilled water being formed as a by-product. This syrup was combined with ground feed grains, the syrup acting as both a binder for pelletizing same, as well as containing the sterilized, cooked nutritive values of the municipal waste and the nutritive values of the yeasts in the fermentation residuum, which yeasts multiplied, of course, during the fermentation step.

I claim as my invention:

1. The process for preparation of useful materials, including liquid fuels, from solidous municipal waste which comprises the steps of:
   (a) Separation of the metal materials present in said waste;
   (b) Separation of the non-friable plastic, hydrocarbon impregnated paper and leather present in said waste;
   (c) Separation of friable materials, as plastics, glass, bone from said waste;
   (d) Steeping to swell water-hydrolyzable material;
   (e) Flotation separation of hydrolyzable from nonhydrolyzable material;
   (f) Fine grinding of the hydrolyzable material;
   (g) acidcatalyzed hydrolysis and saccharification of at least part of the hydrolyzable material to form fermentable sugars;
   (h) Filtration of solublized material of step (g), with recycle of the non-solubles to the hydrolysis step and transfer of the solublized material to the fermentation step;
   (i) pH adjustment to about 3.4 and fermentation;
   (j) Filtration of the fermented mixture, recycling of solid material to the hydrolysis step;
   (k) Distillation to produce (I) Liquid Fuel and (II) Residue suitable for use as plant- and animal-nutrients.

2. The process of claim 1, wherein the product is an oxygenated hydrocarbon derivative.

3. The process of claim 1, wherein the liquid product is a fuel suitable for use in a combustion engine.

4. The process of claim 1, wherein the liquid fuel product is an alcohol.

5. The process of claim 1, wherein the liquid product is an oxygen derivative of a lower hydrocarbon.

6. The process of claim 1, wherein the product nutrient is an animal food.

7. The process of claim 1, wherein the product nutrient is a plant food.

8. The process of claim 1, wherein the product nutrient is a culture medium for micro-organisms.

* * * * *